US005403956A

United States Patent [19]
Pagani

[11] Patent Number: 5,403,956
[45] Date of Patent: Apr. 4, 1995

[54] PROCESS FOR UREA PRODUCTION

[75] Inventor: Giorgio Pagani, Milan, Italy

[73] Assignee: Urea Casale, S.A., Lugano-Besso, Switzerland

[21] Appl. No.: 41,944

[22] Filed: Apr. 2, 1993

[51] Int. Cl.6 ............................................. C07C 273/04
[52] U.S. Cl. ....................................... 564/67; 564/66; 564/70; 564/72
[58] Field of Search ......................... 564/67, 70, 72, 66

[56] References Cited

U.S. PATENT DOCUMENTS

| 4,354,040 | 10/1982 | Inou et al. | 564/67 |
| 4,670,588 | 6/1988 | Zardi | 564/72 |

FOREIGN PATENT DOCUMENTS

| 0479103 | 4/1992 | European Pat. Off. |
| 1573707 | 4/1969 | France |
| 1643092 | 3/1967 | Germany |

*Primary Examiner*—Shailendra Kumar
*Attorney, Agent, or Firm*—Ostrolenk, Faber, Gerb & Soffen

[57] ABSTRACT

A process is described for the industrial synthesis of urea, making the ammonia ($NH_3$) and the carbon dioxide ($CO_2$) react, in at least one reaction space, at high pressures and temperatures and recycling at least in part the unreacted products obtained in a recycle section, characterized by: a) a synthesis reaction between reactants of high purity; and b) a synthesis reaction between less pure reactants, substantially recycled by the so-called recycle section.

The corresponding new plant includes a reactor (R1) of high yield ("once through"), a reactor (R2) of lower yield and a section of recovery and recycle.

The application of the process to preexisting plants requires the simple addition of a reactor of high yield and of pumping devices.

8 Claims, 3 Drawing Sheets

PROCESS FOR UREA PRODUCTION

BACKGROUND OF THE INVENTION

The present invention concerns a process for the industrial synthesis of urea, making ammonia and carbon dioxide react in at least one reaction space, at high pressure and temperature, and recycling at least partially the unreacted products.

The invention also concerns the applications of this process to conventional systems in order to improve the urea yield and reduce energy consumption.

New or modified plants obtained by the implementation of the above-mentioned process and its applications to pre-existing systems are within the scope of the invention.

Several types of processes, systems and plants for the industrial synthesis of urea from $NH_3$ (in excess) and $CO_2$, with recycling after stripping, are known. Among the most prominent of these is the Snamprogetti process of isobaric stripping with $NH_3$.

The main technical characteristics of the isobaric stripping process (Snamprogetti) can be summarized as follows:
synthesis pressure: approx. 150 bar
$NH_3/CO_2$ mol in the reactor: approx. 3.2–3.4
$H_2O/CO_2$ mol in the reactor: approx. 0.6–0.7
temperature of the reactor: 190° C.
yield: approx. 62–63%
steam compumption: approx. 900 kg/MT urea Among the other processes with separate recycle of $NH_3$ widely used in the past, those of Toyo Engineering Ltd., indicated with the abbreviation TRC - TRC-I (Total Recycle C, TRC Improved), can be mentioned, characterized by the fact that the ratio $NH_3/CO_2$ in the reactor is equal to approx. 4–4.5 mol and the separation of $NH_3$ at 18–20 bar is more impressive than the previous process (Snamprogetti), also for the lack of an isobaric stripping.

Another generation of processes has been developed recently for increasing the yield in the reactor of the so-called stripping processes (Snamprogetti $NH_3$ self-stripping and Stamicarbon $CO_2$ stripping), of the conventional values 55–65% up to 70–75%, providing at the same time the above-mentioned high-yield reactors with isobaric loops.

Reference is made to the new and more recent processes such as "IDR" (Isobaric Double Recycle) of Montedison and "ACES" of Toyo Engineering Ltd. The Snamprogetti and the above-referred to prior art processes are described in an article by Zardi in "Nitrogen", No. 135, January/February 1982, pp. 26–37.

In the above-mentioned recent processes "IDR" and "ACES", still operating with high ratios $NH_3/CO_2$ in the high yield reactor, all the unaltered reactants, including the high excess of $NH_3$, are recycled to the reactor under the form of carbamate solution. (The separate recycling of $NH_3$ does not exist.)

Without doubt, much better yields are obtained (compared with the very first processes), but these advantages are coupled with a high complexity and complications in the construction of the equipment.

Furthermore, these processes have the inconvenience of having to strip the unreacted products under high temperature conditions with real risks of decomposition of the laboriously produced urea.

It is worth mentioning that in U.S. Pat. No. 4,670,588, a process with two reaction zones or reactors in series is described, the philosophy of which is, however, completely different from the one of the present invention.

Also in the "IDR" it is possible to utilize reactors with two isobaric zones in series functioning with diverse molar ratios of the reactants.

The first aim of the present invention is to provide a process without the above-mentioned inconveniences which can be operated easily, with total high yields and low consumptions.

Another aim of the invention is the applicability of this process to the conventional systems already having recycling sections for ammonia (or adapted with a new recycling section of the ammonia), reaching global yields of urea transformation in the synthesis sections equal or higher to the ones obtained with the modern processes "IDR", "ACES", etc.

A further aim of the invention is represented by the simple and effective plants (new or modified) resulting from the implementation of the process.

SUMMARY OF THE INVENTION

These and other aims are obtained with the process according to the invention characterized by a) a synthesis reaction between reactants of high purity; and b) a synthesis reaction between less pure reactants, substantially recycled by a recovery section.

The application of this process to conventional systems with recycling of ammonia is characterized by the simple addition of one high yield reactor as well as the devices for the additional pumping of reactants at the operative conditions of synthesis a).

This invention provides a process of producing urea comprising reacting high purity ammonia and carbon dioxide in a first reaction space at high temperature and pressure to produce a first reaction mixture; withdrawing the first reaction mixture from that reaction space and feeding it into a urea recovery section; recovering urea, high purity ammonia and a mixture including an aqueous carbamate solution from the recovery section; introducing the recovered mixture into a second reaction space and reacting it therein to produce a second reaction mixture; withdrawing the second reaction mixture from the second reaction space; and recycling it to the recovery section.

The recovered high purity ammonia is preferably recycled to the first or second reaction spaces. High purity carbon dioxide may also be fed into the second reaction space with or without the high purity ammonia.

In a preferred embodiment of the process, the reaction in the first reaction space is carried out at pressures of from 250 to 450 bar and at temperatures of from 200° to 230° C.; and, in the second reaction space, at pressure of from 130 to 200 bar and at temperatures of from 180° to 200°. The reaction in the first reaction space preferably takes place in the substantial absence of water.

It is preferred that the first and second reaction spaces account for 80 to 20% and 20 to 80%, respectively, of the total urea produced.

SHORT DESCRIPTION OF THE DRAWINGS

In the drawings appended hereto:
FIG. 1 illustrates the prior art Snamprogetti process.
FIG. 2 is a diagrammatic illustration of the process of this invention.
FIG. 3 illustrates the process of this invention applied to the prior art Snamprogetti process.

DETAILED DESCRIPTION OF THE INVENTION

Figure 1:
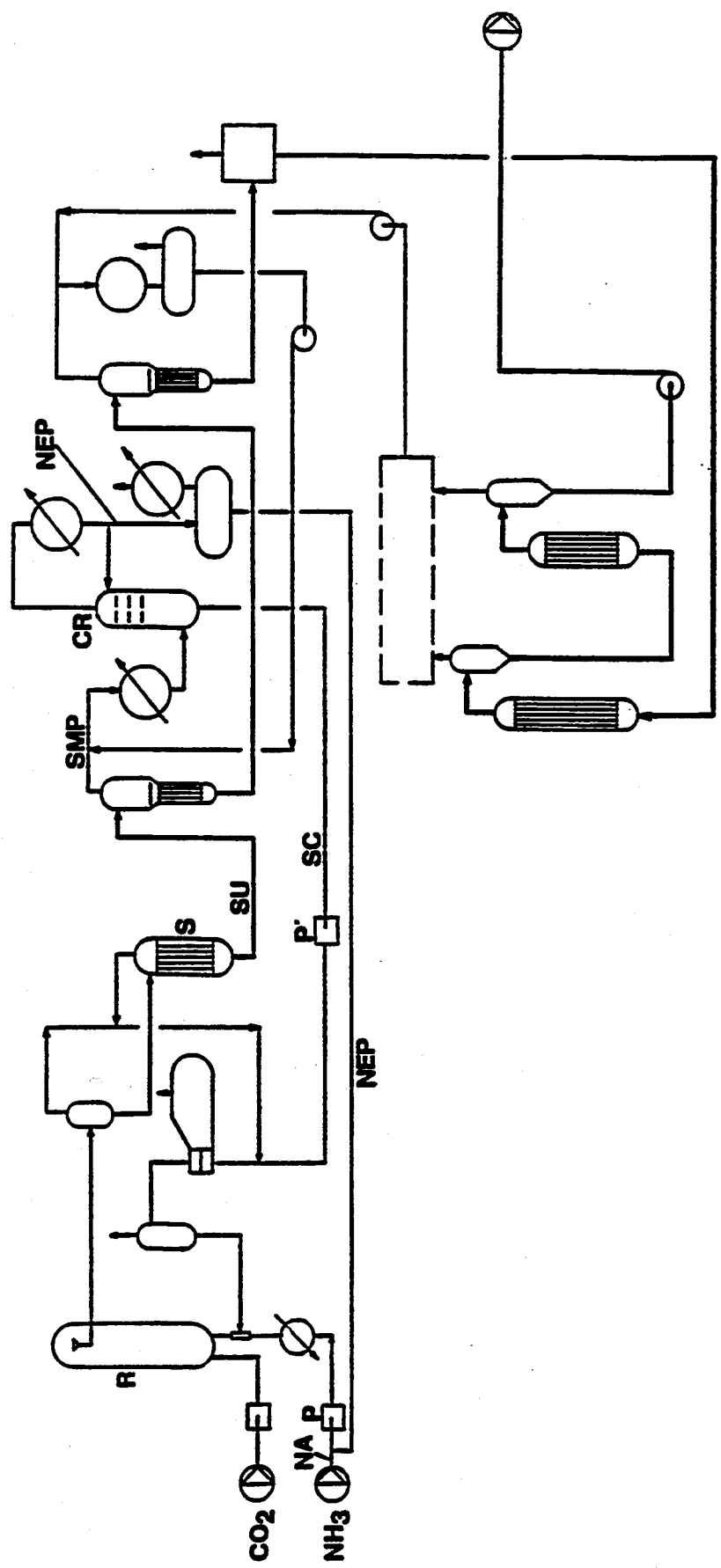

Referring to FIG. 1, which illustrates the prior art Snamprogetti process, in the stripper (S), a great part of the carbamate included in the urea solution coming out of the reactor (R) and part of the free $NH_3$ present are stripped and recycled into the reactor, while a urea solution (SU) leaves the stripper (S) having a relatively low content of residual $CO_2$ (5–7% weight) and containing a relatively high content of $NH_3$ (22–25% weight). This solution (SU) is treated in a middle pressure phase (SMP) where it is distilled at 18–20 bar, and the obtained vapors are sent to a rectification column (CR), enabling the obtention of, first, $NH_3$ at high purity (NEP), and then carbamate solution (SC).

The $NH_3$ at high purity, after condensation, joins the $NH_3$ feed (NA) and is pumped (pump P) into the reactor (R), and the same thing happens with the carbamate solution (pump P').

Figure 2:
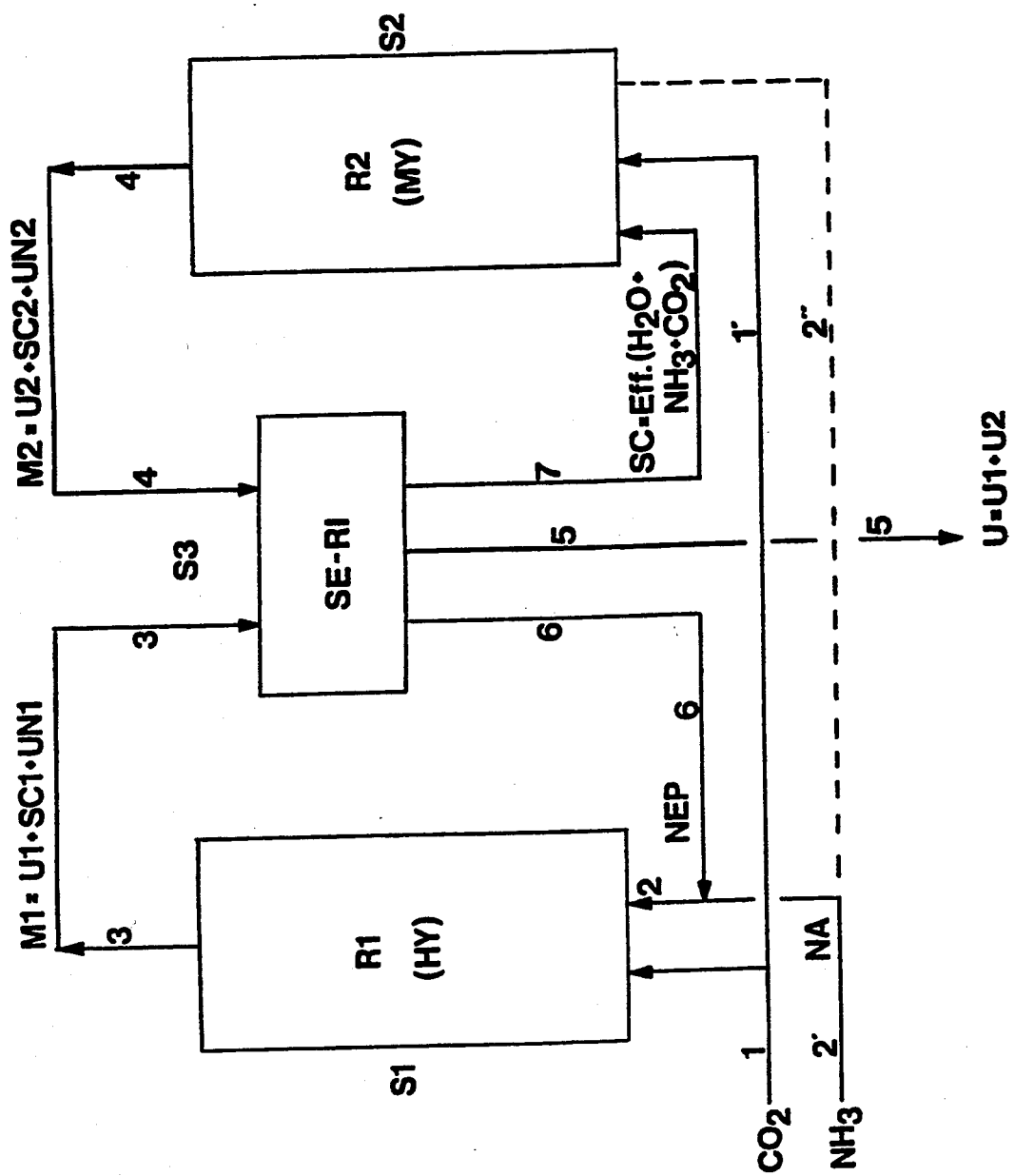

FIG. 2 makes clear the different aspects and advantages of the present invention as exemplified by the preferred embodiment. The plant therein illustrated for the implementation (particularly ex-novo) of the process according to the invention is characterized at least by a first reactor (R1) of high yield (HY) fed with fresh $CO_2$ and $NH_3$ from the outside and with $NH_3$ of high purity from recovery; a second reactor (R2) in parallel with the first one (R1) of yield lower than the first one and fed substantially with reactants from the recovery mixture; and a system or recovery section of the reactants from the reaction mixture obtained from the first and second reactors.

The process can be represented schematically as essentially constituting three sections, two of reaction S1 and S2 of differentiated yield and the last one of recycling SE-RI (S3). S1 includes the reactor R1 fed, characteristically, only (or substantially only) with pure reactants $CO_2$ (line 1) and $NH_3$ (line 2). Receiving only reactants of high purity, R1 is to be considered immediately as reactor of high yield (HY).

The mixture M1 of the reaction products in R1 (HY), made up substantially of urea U1, of the carbamate solution SC1 and the unreacted compounds UN1 (principally $NH_3$ fed in excess from line 2'), is brought from line 3 to recycling section SE-RI, to which is made flow into, through line 4, the same mixture M2 of the products from the reaction in the second reactor R2, mixture made up of urea U2, of carbamate solution SC2 and of unreacted compounds UN2 (principally $NH_3$ fed in excess). From the said recycling section SE-RI, outflow: 1) on line 5, all the produced urea (U) resulting from the partial ones (U1) and (U2) obtained in the two respective reactors R1 and R2; 2) on line 6, ammonia of high purity NEP which, according to a feature of the invention, is recycled again only into reactor R1 together with $NH_3$ fed from the outside (line 2'), having NEP (6) purity substantially compatible with the last one (NA); c) on line 7, the aqueous effluent SC=Eff. ($H_2O + NH_3 + CO_2$), i.e., the mixture consisting in the carbamate aqueous solution and $NH_3$ in excess.

Characteristically, the last aqueous effluent (SC) rich in $NH_3$ of low purity grade and containing $CO_2$, is recycled, through line 7, only into reactor R2 which, receiving reactants less pure than the ones fed into R1, has an average yield (MY), i.e. inferior to the one of R1 (HY).

R2 received fresh $CO_2$ from feeding 1 on line 1' and eventually additional quantity of fresh $NH_3$ on line 2''.

The applications of the process, according to the invention, to the conventional systems with separate recycling of $NH_3$ in order to improve substantially the performances are of particular importance.

Figure 3:
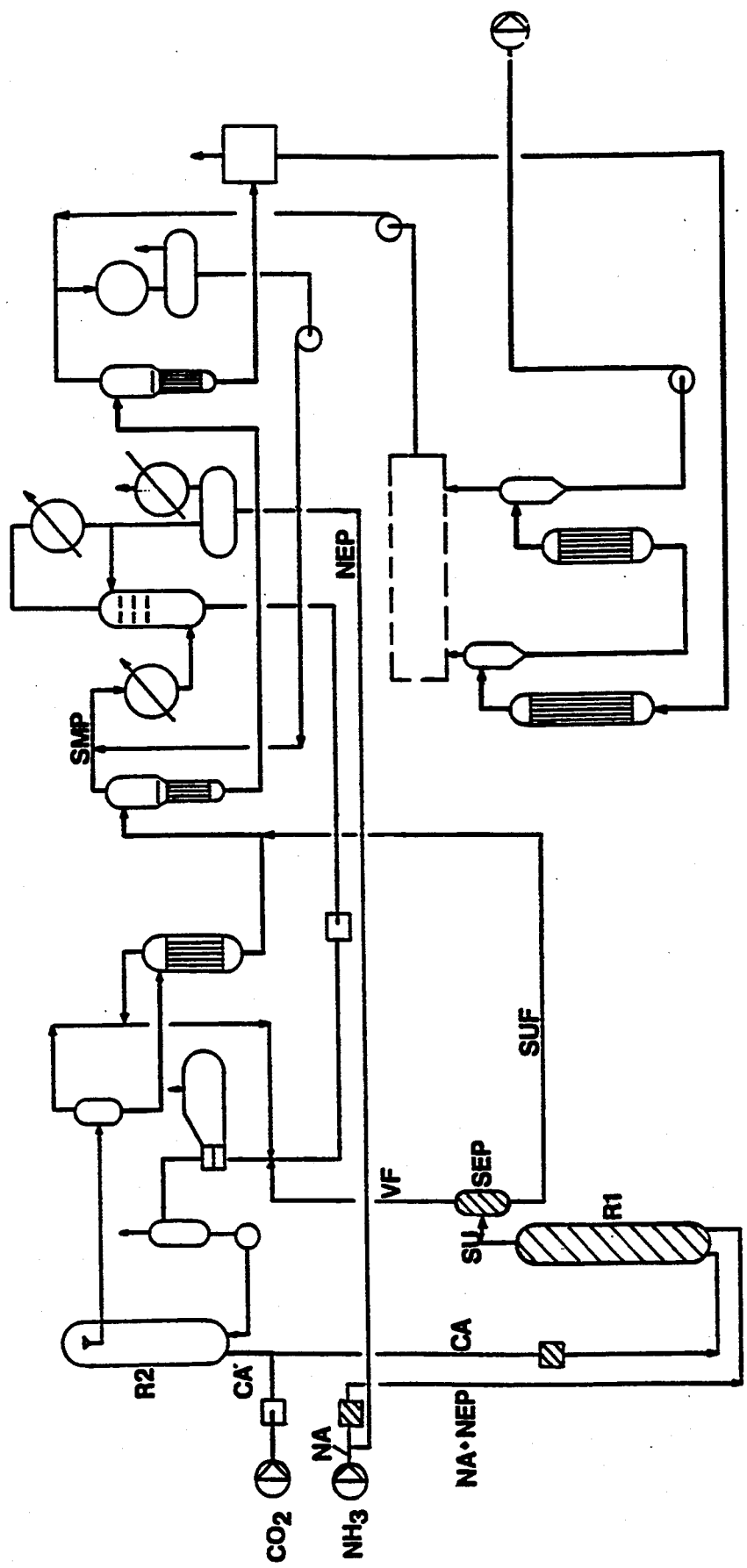

As a not limitative example, we describe in FIG. 3 the application to the $NH_3$ selfstripping process of Snamprogetti.

Such a process, as are most of the urea processes used actually on industrial scale, is of the total recycling type, which means that unreacted $NH_3$ and $CO_2$ coming out of the reactor (or out of the isobaric stripper) are recycled to the reactor in the form of aqueous solution. The presence of recycled $H_2O$ in the reactor reduces the yield of carbamate conversion into urea, penalizing the capacity and the consumption of the plant.

On the other side, it is known that by feeding a synthesis reactor with only pure reactants ($NH_3$ and $CO_2$) we can obtain very high yields. For example in the process known as "Vulcan" (now abandoned) the following results are reached:

$NH_3/CO_2$ in the reactor: 4.5
$H_2O/CO_2$ in the reactor: 0
P: 400 bar
T: 215° C.
yield: 80%
Volume of reactor: 0.05 m3/td urea It is to be noted that the above mentioned values have been reached (and still can be reached) for years on industrial scale in synthesis reactor lined with zirconium, against corrosion. This system has been abandoned because the recovery of residual reactants not transformed in the reactor was complex and uneconomical, by means of a selective chemical separation in order to obtain $NH_3$ of high purity to recycle into the reactor.

According to the present invention (see FIG. 3), the excess of separated ammonia (NEP) in the recycling sections of the Snamprogetti process (or in processes Toyo TRC and TRC-I), together with fresh feeding ammonia (NA), is fed (NA+NEP) into the reactor (R1) of very high yield "once through", for example, of the "Vulcan" type, operating with pressures above 300 bar and temperature above 190° C., where it is transformed into urea together with part of the fresh $CO_2$ (CA) fed in the stoichiometric quantity required for reaching the desired ratio $NH_3/CO_2$ higher than 4. In the conventional reactor (R2) employed in the Snamprogetti scheme, which operates with pressure lower than 300 bar and at temperature lower or equal to 190° C., urea is synthesized by reacting the only carbamate recycle (SC) together with the remaining part of fresh $CO_2$ (CA') the latter being fed into said reactor in such quantity as to maintain in it ratios $NH_3/CO_2$ lower than 4.

In a preferred embodiment form, the new plant for obtaining the transformation of reactants into urea with very high yields includes two reactors in parallel. The first reactor works as "one through" (without recycles) at high pressure (from 250 to 450 bar) and temperatures between 200°–220° C., fed substantially with ammonia and pure $CO_2$. The second reactor works at lower pressure, for example 130–200 bar and lower temperatures, for example 180°–200° C. (better if lower than 190° C.). The reactors are coupled with a total recycle system. Part of the fresh reactants is not sent into the first reactor. All the recycle of the total recycle system is utilized.

In particular, the solution of urea (SU) coming out of the reactor (R1) is preferably expanded in the separator (SEP) operating at reactor pressure (R2) and the freed flash vapours (VF) are sent into the reactor (R2) while the solution of flash urea (SUF) is sent into the section at medium pressure (SMP) for the recovery of the unreacted substance ($NH_3$ and $CO_2$).

With this system, in the above mentioned reactors (R1 and R2 respectively), yields of transformation into urea are reached, in the first one superior from 75 to 85% and in the second one from 60 to 70%; therefore, the yield of combined transformation of the synthesis system is very high depending from the optimal distribution of load between the two reactors.

As already anticipated, the advantage of the process according to the invention is that it can be conveniently used for the realization of new production plants of high yields and low energy consumption as well as for the improvement of urea processes with separate recycle of $NH_3$, for example, of Snamprogetti type (FIG. 3) or Toyo Engineering Ltd.

As already mentioned, a plant modernized by the application of the invention to conventional systems is characterized by the addition of one reactor of high yield R1 and of the devices for bringing the reactants to the higher operative conditions of R1 compared with the old reactor R2.

A new plant is obtained simply by the implementation of the process scheme according to FIG. 2.

EXAMPLE 1

An example referred to the Snamprogetti process (see scheme of FIG. 3) is given hereunder: the recycle $NH_3$ of high purity (NEP) which is pumped into the reactor is 0.4 (*) times the stoichiometry feeding $NH_3$ (NA).

Feeding with totals $NH_3$ (NA+NEP) the parallel reactor R1 (high efficiency parallel converter HY) type "once through" proposed by the present invention, we have:

| | |
|---|---|
| available $NH_3$: | $\approx$ 1.4 × 570 = 798 kg/t urea = |
| | 46.94 kmol/t urea |
| $NH_3/CO_2$: | 4.5 mol |
| necessary $CO_2$: | $\frac{46.94}{4.5}$ = 10.43 Kmol/t = 459 kg/t |
| $H_2O/CO_2$: | 0 |

With an obtainable yield of 80%, the $CO_2$ transformed into urea is:

$$459 \times 0.8 = 367.2 \text{ kg/t} = 367 \frac{60}{44} = \approx 500 \text{ kg urea/t urea}$$

It is therefore possible to produce approx. 50% of the urea in reactor R1, i.e. in high yield conditions. (*) to be noted that in the Snamprogetti plants the recycle $NH_3$ of high purity can vary from 0.3 to 0.5 times the feeding and more, while in the following example, absolutely not limitative of the invention, an average value of 0.4 has been presumed.

A Snamprogetti plant with reactors in parallel of high yield (HY) will therefore operate with an average yield equal to approx.

$$\frac{63 + 80}{2} = 71.5\%$$

and the steam consumption will consequently be notably reduced (550–600 kg/t urea against the conventional value of 900 kg/t).

The invention is susceptible to all these variants and modifications which, for being within easy reach of a skilled person, have to be considered as falling within the scope and spirit of this invention.

I claim:

1. A process of producing urea comprising the steps of reacting high purity ammonia and carbon dioxide in a first reaction space at high temperature and pressure to produce a first reaction mixture, withdrawing said first reaction mixture thus obtained and feeding it into a urea recovery section, recovering high purity ammonia and a mixture including an aqueous carbamate solution from said urea recovery section, introducing said recovered mixture into a second reaction space and reacting it therein to produce a second reaction mixture;

withdrawing said second reaction mixture from said second reaction space and recycling it to said recovery section.

2. A process according to claim 1, comprising the additional step of recycling to said first and/or second reaction spaces high purity ammonia separated in the recovery section.

3. A process according to claim 1, wherein the step of urea synthesis in the first reaction space accounts for 80 to 20% of the total urea produced.

4. A process according to claim 1, further comprising the step of feeding high purity carbon dioxide and optionally high purity ammonia to said second reaction space.

5. A process according to claim 1, wherein step of urea synthesis in the second reaction space accounts for 20 to 80% of the total urea produced.

6. A process according to claim 2, wherein urea synthesis in the first reaction space takes place in substantial absence of recycle water.

7. A process according to claim 1, wherein the urea synthesis in the first reaction space is carried out at pressures of from 250 to 450 bar and at temperatures of from 200° to 230° C.

8. A process according to claim 1, wherein the urea synthesis in the second reaction space is carried out at pressures of from 130 to 200 bar and at temperatures of from 180° to 200° C.

* * * * *